United States Patent
Hintersehr

(10) Patent No.: US 6,660,400 B1
(45) Date of Patent: Dec. 9, 2003

(54) DENTAL PROSTHESIS BLANK

(75) Inventor: Josef Hintersehr, Griesheim (DE)

(73) Assignee: Hint-Elc CmbH, Griesheim (DE)

( * ) Notice: Subject to any disclaimer, the term of this patent is extended or adjusted under 35 U.S.C. 154(b) by 147 days.

(21) Appl. No.: 09/618,146

(22) Filed: Jul. 17, 2000

(30) Foreign Application Priority Data

Jul. 16, 1999 (DE) .......................................... 199 32 877

(51) Int. Cl.$^7$ ............................ B29B 7/00; B29B 11/00; B29B 15/00; A61C 8/00; A61C 13/08
(52) U.S. Cl. .................. 428/542.8; 428/34.1; 433/167; 433/201.1; 433/202.1; 206/63.5
(58) Field of Search .......................... 433/201.1, 202.1; 604/259; 206/63.5; D24/152–156, 176–181; 428/34.1, 542.8

(56) References Cited

U.S. PATENT DOCUMENTS

| | | |
|---|---|---|
| 4,615,678 A | 10/1986 | Moermann et al. |
| 5,342,696 A | 8/1994 | Eidenbenz et al. |
| 5,362,237 A * | 11/1994 | Chalifoux ................... 433/220 |
| 5,939,211 A * | 8/1999 | Mormann ................. 428/542.8 |
| 6,482,284 B1 * | 11/2002 | Reidt et al. .................. 156/200 |

FOREIGN PATENT DOCUMENTS

| | | | |
|---|---|---|---|
| DE | 33 12908 | * | 4/1983 |
| DE | 197 33 161 | | 2/1999 |
| EP | 0 759 728 | | 10/1997 |
| WO | WO 99/29255 | * | 6/1999 |

* cited by examiner

Primary Examiner—Harold Pyon
Assistant Examiner—Brian P. Egan
(74) Attorney, Agent, or Firm—Jacobson Holman PLLC

(57) ABSTRACT

A dental prosthesis blank and a combined dental prosthesis blank and blank holder. The dental prosthesis blank provides for forming a dental prosthesis therefrom and the blank holder holds the blank during the forming of the prosthesis. The blank comprises a first free end for forming the dental prosthesis therefrom and a positioning end for positioning the blank in the blank holder. The positioning end includes a cylindrical cone, i.e. extension, having a pair of reference surfaces defined by a slot extending along the axis of the cylindrical extension. The blank holder includes a reference element such as a bar that fits within the space between the reference surfaces.

16 Claims, 4 Drawing Sheets

DENTAL PROSTHESIS BLANK

FIELD OF THE INVENTION

The invention relates to a dental prosthesis blank, whose end, which is not to be cut, is connected to an essentially cylindrical cone, and a blank holder with radially moveable gippers for the dental prosthesis blank.

A dental prosthesis blank, as disclosed, for example, in the EP A 759 728, is made of a precious metal, a titanium alloy, or a sintered zirconium oxide or the like. Usually it exhibits a cylindrical body, to which a cone is molded that is also cylindrical and that usually tapers off radially. To be able to cut the individual dental prosthesis from the body, the blank must be clamped so as not to rotate in a blank holder during the machining process. As soon as the machining is completed, the blank is removed from the holder, whereby the dental prosthesis is still attached to a body stump.

It can happen that, after the dental prosthesis has been accurately measured, it is necessary to rework it; and, therefore, the blank must be clamped again into the holder. The subsequent work is usually done by hand, a state that requires not only considerable skill, but also does not often lead to the desired result Therefore, the invention is based on the problem of simplifying the reworking of a dental prosthesis connected to the body trunk of a blank.

SUMMARY OF THE INVENTION

To this end, the invention provides for the aforementioned blank that the cone exhibits at least one reference element, which interacts with a spatially fixed reference counter element so as to position accurately the blank in the circumferential direction when clamping the cone into a blank holder. The reference element and the reference counter element form a spatial reference system, which always spatially fixes the blank, inserted into the blank holder, in a precisely specified circumferential direction around the blank axis so that, when the dental prosthesis is being machined out of the blank body, the blank can be inserted arbitrarily often into the holder and removed again from the same without thus changing the spatial position of the dental prosthesis. Therefore, it is possible to easily rework the dental prosthesis with the necessary accuracy.

In the preferred embodiment of the invention the reference element is a flat reference surface, which extends expediently parallel to the axis of the cone. An especially preferred embodiment of the invention provides that the cone is slit axially; and the reference element is formed on or in the slit. Here it is especially recommended that one flat reference surface be formed at each of the two side walls that belong to the slit and lie opposite the axis of the cone. The reference counter element can be a free leg or a rib, which is formed in the blank holder. Said reference counter element extends at right angle to the cone's direction of insertion into the holder and has a radial width, which is equivalent to precisely the distance between the two reference surfaces on the slit cheeks. Thus, the slit floor, connecting the two reference surfaces, can serve as the axial reference, which also interacts with the leg or the rib when clamping the blank into the holder.

The accuracy of the blank alignment in the holder in the circumferential direction is increased in another improvement of the invention when the cone is slotted crosswise, whereby the respective cheeks of the cross slots are designed as flat reference surfaces, parallel to the axis.

Moreover, the embodiments of the invention are disclosed in the dependent claims. The invention is described in detail in the following with reference to two embodiments depicted in the attached drawings.

DETAILED DESCRIPTION OF THE INVENTION

Figure 1:
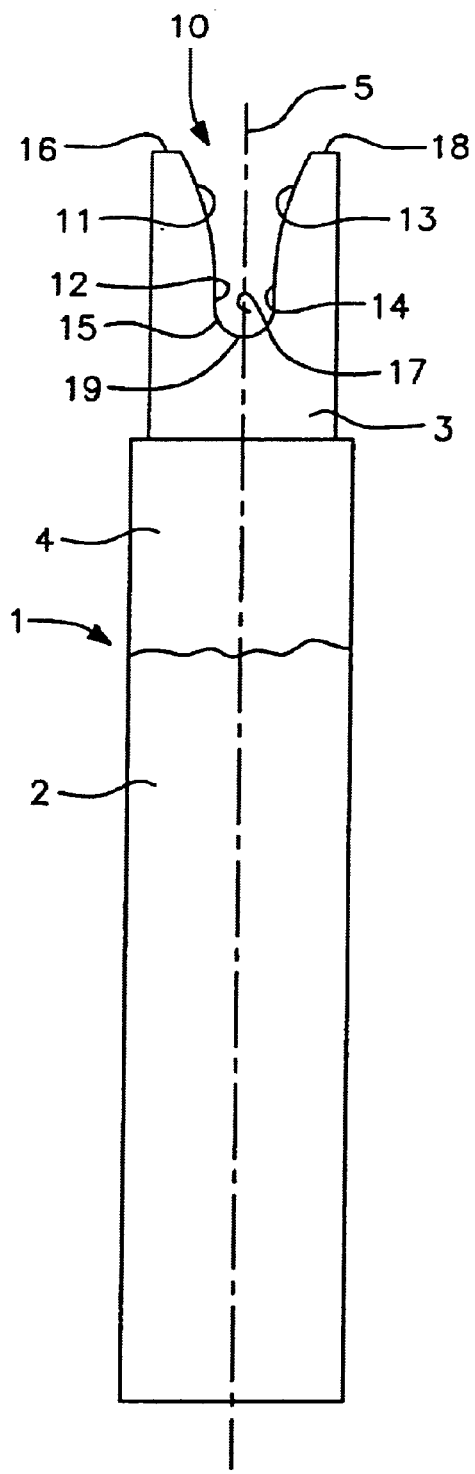
FIG. 1 is a schematic drawing of a first embodiment of the dental prosthesis blank, equipped with the features of the invention.
Figure 2:
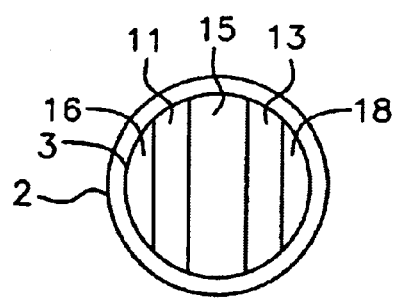
FIG. 2 is a top view of the cone of the blank according to FIG. 1.
Figure 3:
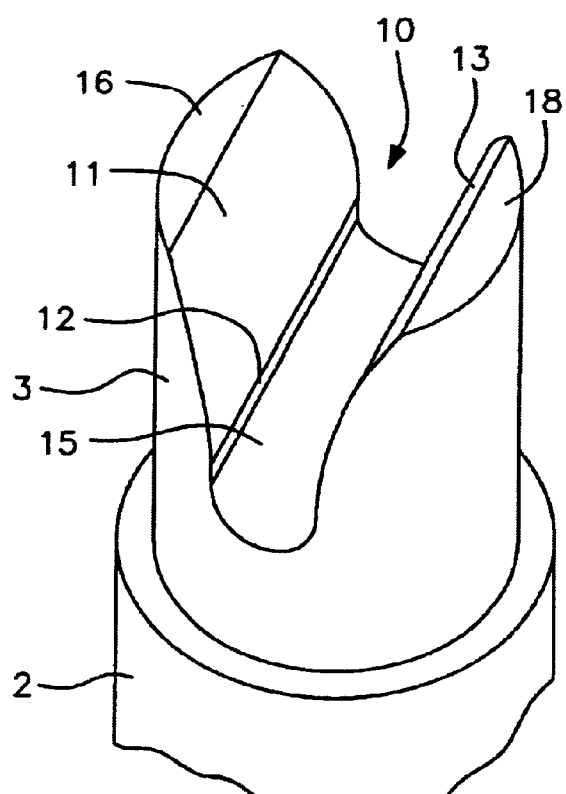
FIG. 3 is a schematic drawing of a perspective view of the cone according to FIGS. 1 and 2.

The dental prosthesis blank 1 comprises a cylindrical body 2, whose end, which is not to be cut, exhibits a cone 3, which is coaxial to the body and exhibits a cylindrical outer contour. Body 2 and cone 3 are made here of the same material or two materials with essentially identical hardness. After clamping a blank 1 into the blank holder, which approximately resembles a collect 90, whose grippers 92, 94, 96 grasp the cone 3 from the outside, an individual dental prosthesis is cut, for example machined, by electroerosive machining, according to specified data, from the front, free end segment of the body 2.

The cone 3 is provided with a straight slot 10 parallel to the axis 5 of the blank 1 starting from its free end. Said slot extends at right angle to the axis 5; and the axis 5 runs through its center. The slot 10 exhibits outwardly bent, opposite flat segments 11, 13, which serve as aids to insert a bar or rib shaped reference element 70 in the collect 90. Attached to the surfaces 11, 13 are two flat reference surfaces 12, 14, which lie opposite each other on the inside and run parallel and symmetrical to the axis 5. Said flat reference surfaces lie a fixed distance apart. The center of curvature 17 of the convexly curved slit floor 15 lies on the axis 5 in the area of the reference surfaces 12, 14.

The reference counter element 70 comprises a cylindrical bar, which extends at right angle to the insertion direction of the cone 3 into the opening of the collect 90. The collect also exhibits two opposing boreholes relative to the insertion direction. Both opposing ends of the bar 70 are held in said boreholes. Its outer diameter is equal to the said distance between the reference surfaces 12, 14. The width of the reference surfaces 12, 14, taken in the direction of the axis 5, and the innermost point 19 of the slit floor 15 are adjusted in such a manner relative to each other that the cone 3 can be inserted into the opening of the collect 90 until the bar 70 moves sideways so as to rest against the reference surfaces 12, 14 and against the point 19. Obviously the cone 3 and thus the dental prosthesis blank is fixed in the collect 90 in both the circumferential and axial direction. This fixing in position can be repeated with an accuracy of about 30µfor example, when reworking the blank That is, when the cone 3 is inserted again into the collect 90, the deviations from the specified position of the blank are no greater than the said value. Moreover, the end (not illustrated) of the collect 90 can be provided, for example, with an outer thread so that it can be screwed into the chuck of a metal cutting machine (not illustrated) for the blank.

Figure 4:
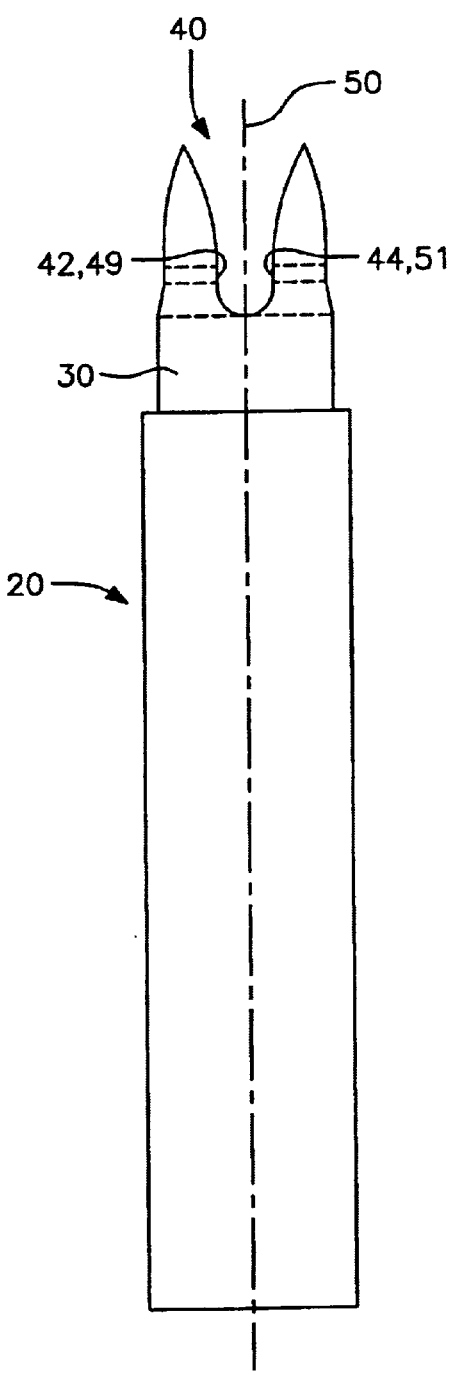
FIG. 4 is is a side view of a second embodiment of a dental prosthesis blank of the invention.
Figure 5:
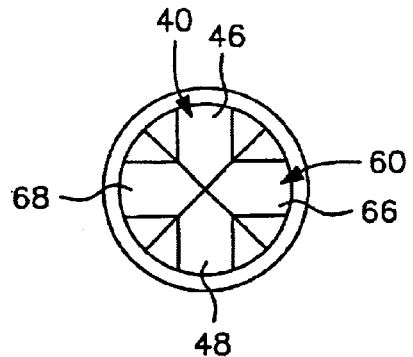
FIG. 5 is is a top view of the cone of the blank according to FIG. 4.
Figure 6:
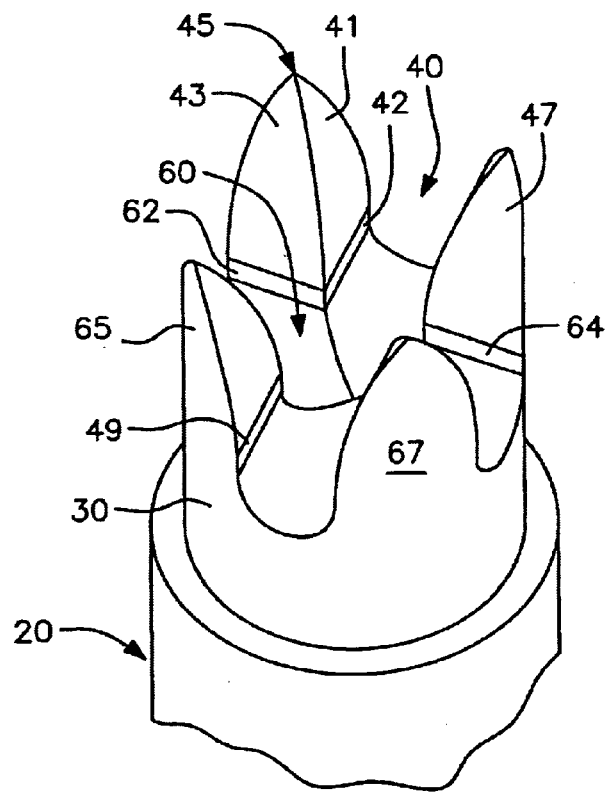
FIG. 6 is a schematic drawing of perspective view of the cone, machined out of the blank and shown in FIGS. 4 and 5.
Figure 7:
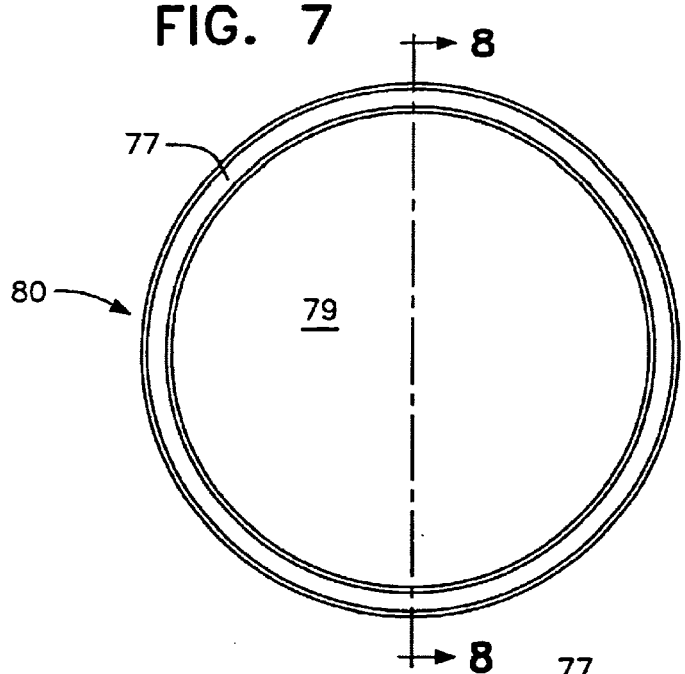
FIG. 7 is a front view of a holder, which exhibits the cone and is intended for the dental prosthesis blank.
Figure 8:
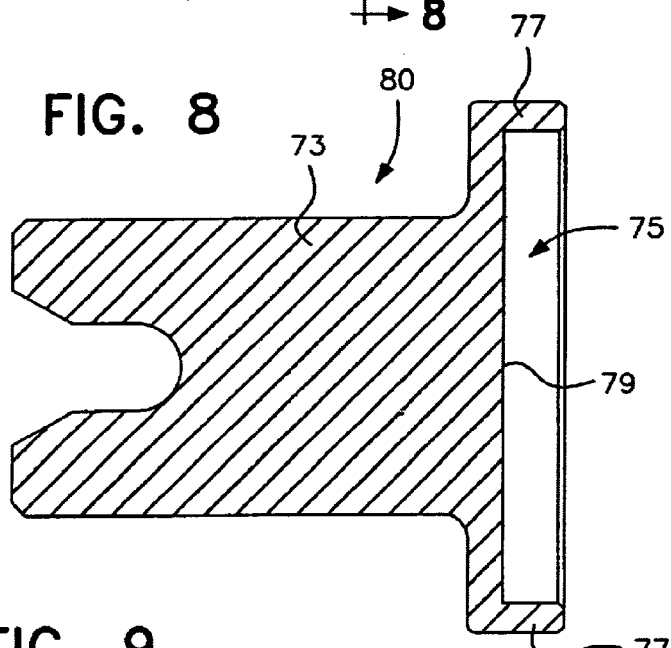
FIG. 8 is an axial view of the holder along line A—A of FIG. 7.

In the embodiments depicted in FIGS. 4 and 6, two slots 40, 60, which lie opposite each other at right angles and cross in the axis 50 of the blank 30, are cut into the cone 30 of the dental prosthesis blank 20, starting from the free front side . In this manner are formed two aligned slotted segments 46, 48, or two aligned slotted Segments 66, 68. Each of the slotted segments 46, 48 and 66, 68 exhibits on its flanks opposing, parallel and flat reference surfaces, which lie symmetrical relative to the longitudional axis of the respective slot 40 or 60. Said reference surfaces resemble the reference surfaces 12, 14, of which FIG. 6 shows the reference surface 42 of the slotted sent 46 and the reference surface 49 of the slotted segment 48 and the reference surface 62 of the slotted segment 68 and the reference surface 64 of the slotted segment 66. According to FIG. 4, the reference surfaces 42, 49 are aligned with the symmetrical flanks of the slotted segments 46,48; and the reference surfaces 44, 51 are aligned with the opposing flanks of the same slotted segments. To engage with the cross slot 40, 60, the chuck of the holder has, of course, a matching ba cross.

Since the shell of the cone 30 is cylindrical, the results of the outwardly curved insertion surfaces 41, 43 are four separate posts 45,47, 65, 67, which taper to a point externally.

Figure 9:
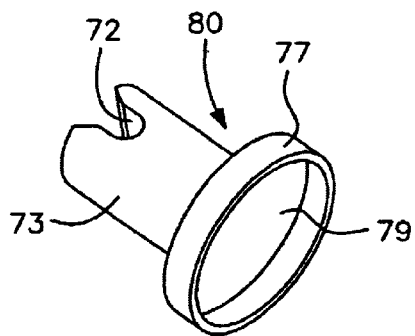
FIG. 9 is is a perspective view of the holder of FIG. 7.

The embodiment of the invention, shown in FIGS. 7 to 10, may be used pray when the material of the body 2 is less hard than that of the cone 3. In this case the body 2 is cemented or welded on the front side of a holder 80, provided with the cone 73. To this end, the holder 80 exhibits at its front side circular pan 75 whose raised rim rums around a floor 79. Into said pan is inserted the body 2. The clear width enclosing the rim is just a little larger than the outside diameter of the cylindrical body, which is to be inserted cone 73 is identical in all of its detail to the cone 3, thus is provided especially with the references surfaces described there. FIG. 9 depicts one of these reference at 72.

Figure 10:
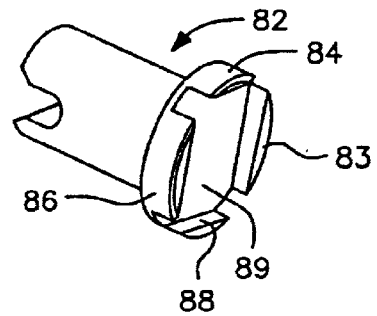
FIG. 10 is a perspective view of a holder for a dental prosthesis blank with a square cross section.
Figure 11:
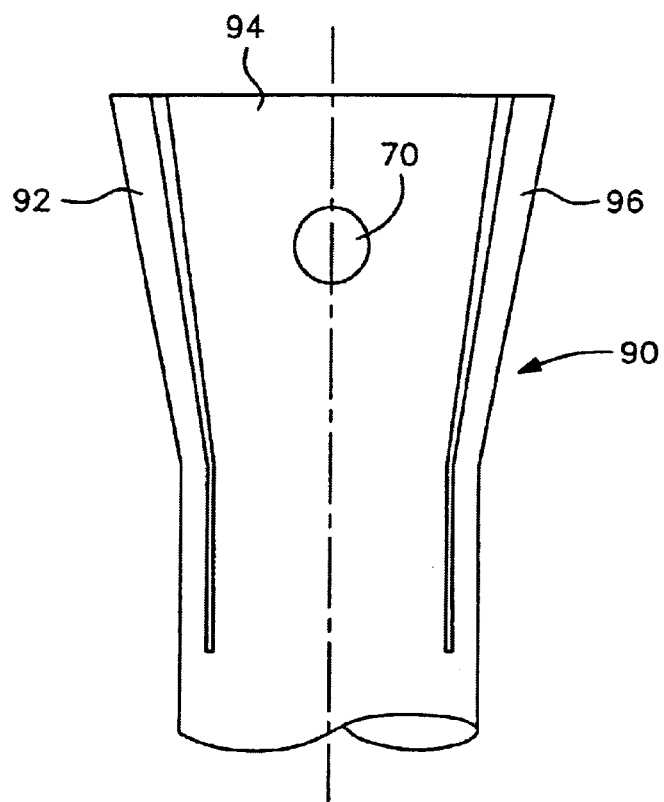
FIG. 11 is is a side view of the head of a collet.
Figure 12:
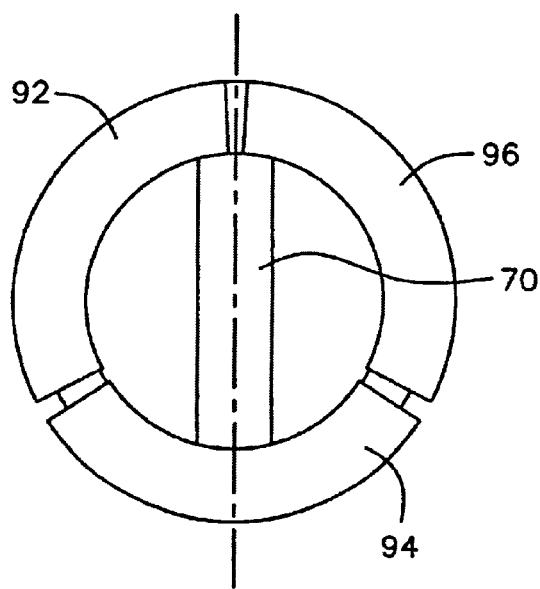
FIG. 12 is is a front view of the collet of FIG. 11.

The holder 82 of FIG. 10 differs from the holder 80 only in the rim is divided into four rim segments 83, 84, 86, 88 which are spaced equidistant apart in the circumferential direction, so At its floor 89 encloses a square area, into which a body with aching square cross section can be inserted and cemented on the floor 89 between the rim segments 83, 84, 86, 88.

What is claimed is:

1. A dental prosthesis blank comprising a first free end machinable to form a dental prosthesis and a positioning end for positioning the blank in a blank holder having a reference element therein, said positioning end of said blank comprising a substantially cylindrically shaped cone having a second free end which includes at least one pair of parallel reference surfaces spaced in opposing relationship, said reference surfaces defining a space therebetween and extending symmetrically and transversely to a rotational axis of said cone, each of said reference surfaces extending entirely across said cone and wherein said space is defined to receive the reference element of the blank holder with the reference surfaces engageable with the reference element of the blank holder to enable repeatable and precise positioning of said blank within the blank holder.

2. A blank as claimed in claim 1, wherein said cone is a unitary part of said blank.

3. A blank as claimed in claim 1, wherein said cone is a separate structure having a seat for receiving and bonding to said blank.

4. A blank as claimed in claim 1, wherein said reference surfaces are flat.

5. A blank as claimed in claim 4, wherein said reference surfaces extend parallel to a longitudinal axis of the cone.

6. A blank as claimed in claim 1, wherein said cone is slotted axially and the reference surfaces are formed by the slot.

7. A blank as claimed in claim 6, wherein said reference surfaces are flat and spaced a specified distance apart in accordance with the thickness of the blank holder reference element.

8. A blank as claimed in claim 6, wherein the axial slot has a convexed slot floor, the center of curvature thereof lying on said rotational axis and between the reference surfaces.

9. A blank as claimed in claim 6, wherein the innermost point of the slot determines the axial positioning of the cone within the blank holder.

10. A blank as claimed in claim 1, wherein two slots are cut into the cone at right angle to said rotational axis to define two pair of reference surfaces.

11. A blank as claimed in claim 10, wherein said two slots lie at right angle to each other.

12. A blank as claimed in claim 10, wherein each of said two slots define an opposing pair of reference surfaces.

13. A dental prosthesis blank for forming a dental prosthesis therefrom and a blank holder means for holding the blank during the forming, said blank comprising;
    a first free end for forming a dental prosthesis therefrom and a positioning end for positioning the blank in said blank holder means, said positioning end having a substantially cylindrical extension having a second free end which includes at least one pair of reference surfaces defined by a slot extending from said second free end along the axis of said cylindrical extension, said reference surfaces defining a space therebetween and extending symmetrically and transversely to said axis and extending entirely across the cylindrical extension for cooperation with a reference element of said blank holder means when clamping the blank to the blank holder means;
    said blank holder means for holding said blank during the forming comprising;
    a reference element having a thickness substantially equal to said space between said reference surfaces wherein said reference element fits into said space and engages said reference surfaces.

14. The blank and blank holder of claim 13 wherein said blank holder means comprises radially moveable grippers for receiving the cylindrical extension.

15. The blank and blank holder as claimed in claim 13 wherein said blank holder means comprises an axially oriented wall portion for receiving said cylindrical extension of said blank, and said reference element comprises a bar which extends at right angles to the axial orientation.

16. The blank and blank holder as claimed in claim 15 wherein the bar defines the axial position of the blank within the blank holder means.

* * * * *

UNITED STATES PATENT AND TRADEMARK OFFICE
CERTIFICATE OF CORRECTION

PATENT NO.     : 6,660,400 B1
DATED          : December 9, 2003
INVENTOR(S)    : Josef Hintersehr It is certified that error appears in the above-identified patent and that said Letters Patent is hereby corrected as shown below:

Title page,
Item [73], Assignee, change "Hint-Elc CmbH" to -- Hint-Els GmbH --;

Column 1,
Line 8, change "gippers" to -- grippers --;
Line 24, add a period at the end of the sentence;

Column 2,
Line 2, change "collect" to -- collet --;

Column 3,
Lines 5, 9 and 11, change "collect" to -- collet --;
Line 7, change "30µfor" to -- 30µ for --;
Line 8, change "blank That" to -- blank. That --;
Line 19, change "side ." to -- side. -- (delete extra space before period);
Line 20, change "Segments" to -- segments --;
Line 26, change "sent" to -- segment --;
Line 33, change "ba" to -- bar --;
Line 39, change "pray" to -- primarily --;
Line 43, after "side" insert -- a --;
Line 43, change "rums" to -- runs --;
Line 47, after "inserted" insert -- . The --;
Line 51, after "in" insert -- that --;
Line 53, delete "At";
Line 54, change "aching" to -- matching --.

Signed and Sealed this

Nineteenth Day of October, 2004

JON W. DUDAS
*Director of the United States Patent and Trademark Office*